(12) United States Patent
Boyes et al.

(10) Patent No.: US 12,208,199 B2
(45) Date of Patent: Jan. 28, 2025

(54) SYSTEM FOR HUMIDIFICATION OF MEDICAL GASES

(71) Applicant: Fisher & Paykel Healthcare Limited, Auckland (NZ)

(72) Inventors: Richard John Boyes, Auckland (NZ); Christian Francis Fischer, Auckland (NZ); Joseph Patrick Walter Strevens, Auckland (NZ); Elmo Benson Stoks, Auckland (NZ); Jayananda Mallinson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 367 days.

(21) Appl. No.: 16/903,190

(22) Filed: Jun. 16, 2020

(65) Prior Publication Data

US 2020/0306464 A1    Oct. 1, 2020

Related U.S. Application Data

(63) Continuation of application No. 15/548,931, filed as application No. PCT/IB2016/050619 on Feb. 6, 2016, now Pat. No. 10,722,663.

(Continued)

(51) Int. Cl.
*A61M 13/00* (2006.01)
*A61B 17/34* (2006.01)
(Continued)

(52) U.S. Cl.
CPC ....... *A61M 13/003* (2013.01); *A61B 17/3474* (2013.01); *A61M 16/0875* (2013.01);
(Continued)

(58) Field of Classification Search
CPC .............. A61M 16/16; A61M 16/0875; A61M 16/145; A61M 16/1095; A61M 16/109; A61M 13/003; A61B 17/3474
(Continued)

(56) References Cited

U.S. PATENT DOCUMENTS 3,119,541 A    1/1964  Lynn
6,096,332 A    8/2000  Yang
(Continued)

FOREIGN PATENT DOCUMENTS

GB          1485458 A    9/1977
WO          WO 98/02199  1/1998
(Continued)

OTHER PUBLICATIONS

UnitConverters.net, "Convert CC to ML", <https://www.unitconverters.net/volume/cc-to-ml.htm>, Sep. 14, 2022.*
(Continued)

*Primary Examiner* — Michael J Tsai
*Assistant Examiner* — Nidah Hussain
(74) *Attorney, Agent, or Firm* — Knobbe Martens Olson & Bear LLP

(57) ABSTRACT

A humidification system has a tube configured to transport gases. The tube is configured to be soaked prior to use and has a bead to hold liquid. Heat applied to the bead causes the liquid to be released as vapour. Gases flowing through the tube are heated and humidified by the vapour.

21 Claims, 9 Drawing Sheets

Related U.S. Application Data

(60) Provisional application No. 62/112,784, filed on Feb. 6, 2015.

(51) Int. Cl.
    *A61M 16/08*     (2006.01)
    *A61M 16/10*     (2006.01)
    *A61M 16/14*     (2006.01)
    *A61M 16/16*     (2006.01)

(52) U.S. Cl.
    CPC ...... *A61M 16/109* (2014.02); *A61M 16/1095* (2014.02); *A61M 16/145* (2014.02); *A61M 16/16* (2013.01); *A61M 2205/3653* (2013.01); *A61M 2210/1017* (2013.01)

(58) Field of Classification Search
    USPC .......................................................... 604/24
    See application file for complete search history.

(56) References Cited

U.S. PATENT DOCUMENTS

| | | |
|---|---|---|
| 6,123,935 A | 9/2000 | Wefler |
| 2004/0102731 A1* | 5/2004 | Blackhurst ........ A61M 16/0493 604/113 |
| 2004/0168690 A1 | 9/2004 | Payne |
| 2005/0166451 A1 | 8/2005 | Stachnik |
| 2007/0104540 A1* | 5/2007 | Howard ................. B09B 1/004 405/128.25 |
| 2007/0219532 A1* | 9/2007 | Karpowicz ............. A61M 1/96 604/540 |
| 2010/0226824 A1 | 9/2010 | Ophir |
| 2014/0180198 A1 | 6/2014 | Ott |
| 2014/0236083 A1 | 8/2014 | Sims |
| 2015/0196323 A1* | 7/2015 | Koeth .................. A61M 16/18 600/560 |
| 2017/0143931 A1* | 5/2017 | Zheng ................. A61M 16/164 |

FOREIGN PATENT DOCUMENTS

| | | |
|---|---|---|
| WO | WO 1998/26826 A1 | 6/1998 |
| WO | WO 2005/000089 | 1/2005 |
| WO | WO 2008/095245 | 8/2008 |
| WO | WO 2010/116846 | 10/2010 |
| WO | WO 2014/088430 | 6/2014 |
| WO | WO 2014/111083 | 7/2014 |

OTHER PUBLICATIONS

Apr. 11, 2016 International Search Report for International Application No. PCT/IB2016/050619 filed on Feb. 6, 2016.

\* cited by examiner

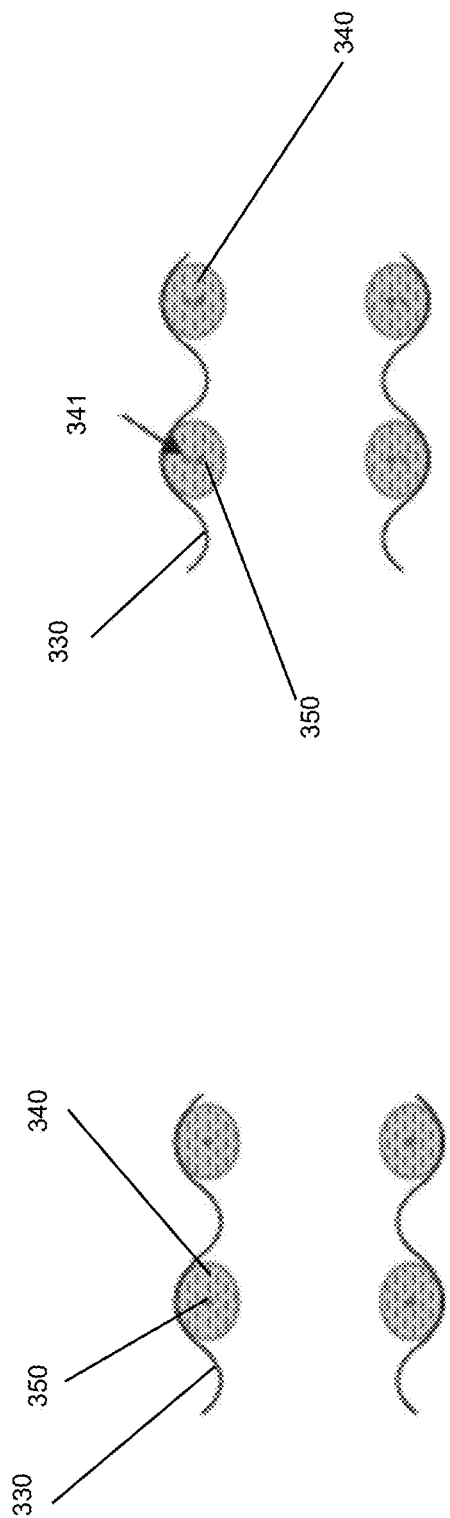
Figure 3E
Figure 3F
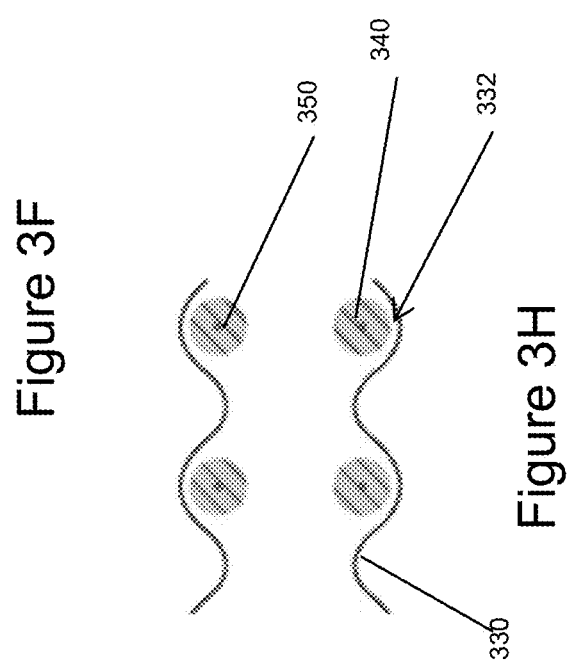
Figure 3H
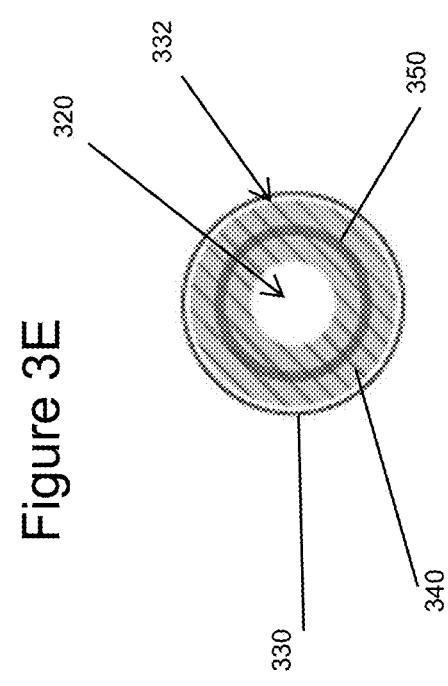
Figure 3G

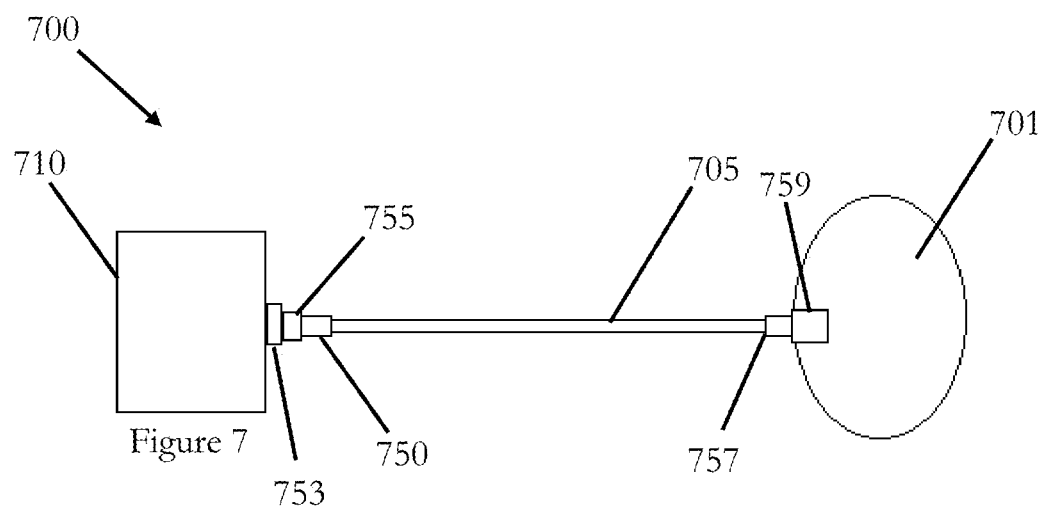
Figure 7
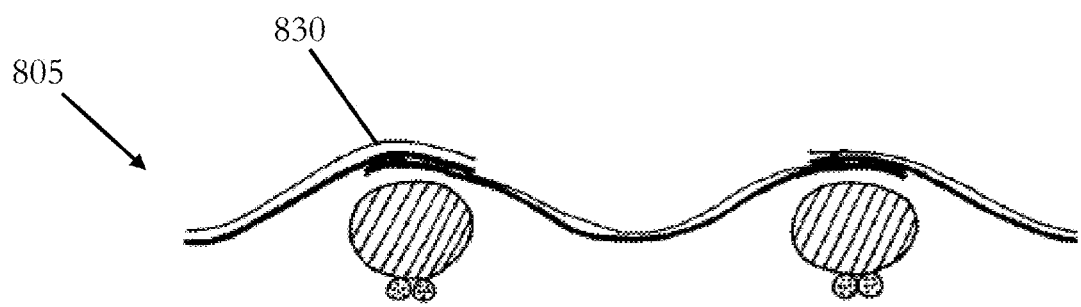
Figure 8

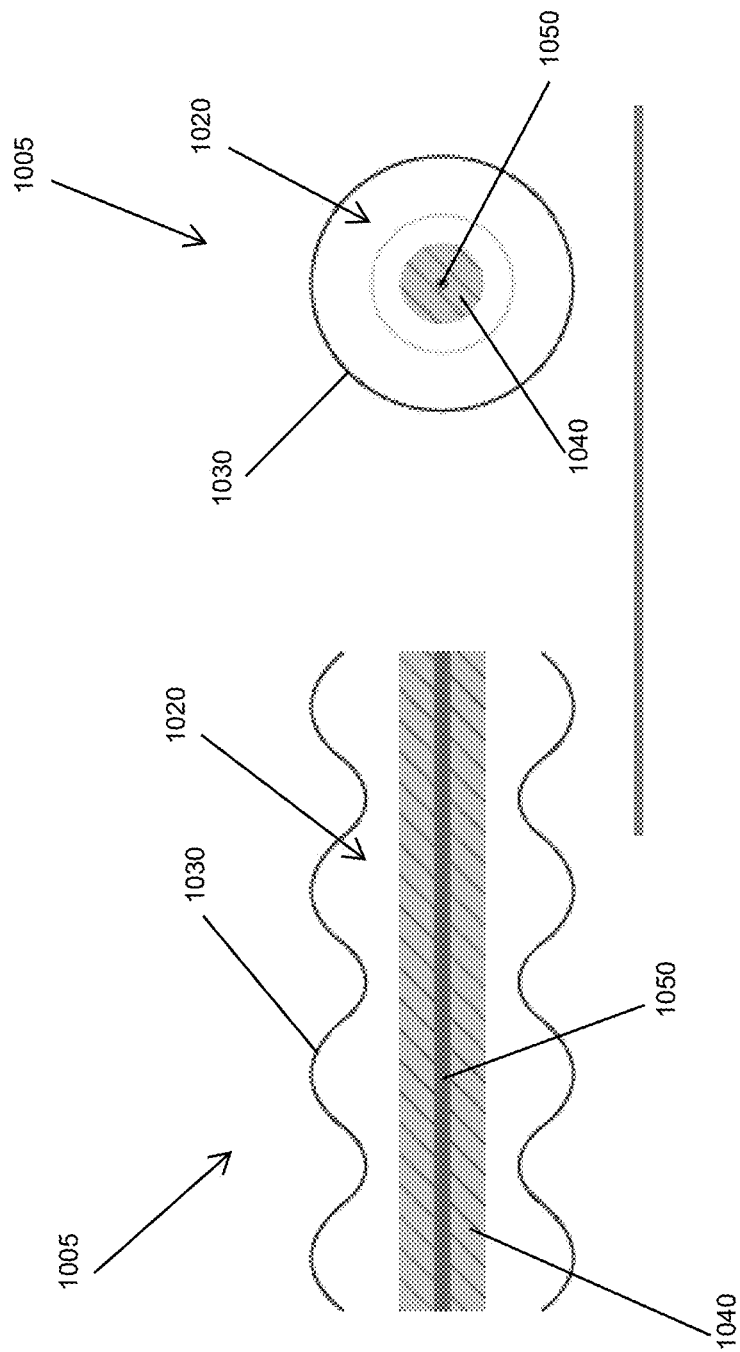

SYSTEM FOR HUMIDIFICATION OF MEDICAL GASES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application hereby incorporates by reference U.S. Prov. App. No. 62/112,784 filed on Feb. 6, 2015 in its entirety.

BACKGROUND

Technical Field

The present disclosure generally relates to a system for the humidification of medical gases More particularly, the present disclosure relates to a system for the humidification of medical gases using an integrated tube humidifier.

Description of the Related Art

A humidification apparatus is used to provide heated and humidified gases to a patient via a patient interface. Humidified medical gases protect the peritoneum from desiccation and inflammation caused by cold dry gases used during surgical procedures.

Pass-over humidification devices supply heated, humidified gases to a patient. Such a humidification system comprises a humidification apparatus, a humidification chamber, a tube system, and a patient interface. The humidification apparatus further comprises a heater plate that is configured to heat the humidification chamber. This causes vapour to form, which enters the gases flow, humidifying the medical gases. Humidification systems can have a large footprint and require large volumes of liquid for humidification to take place. Heat is applied to the heater plate of the humidification chamber to form vapour, meaning the heater plate is hot to touch.

Humidification systems for surgical applications may comprise a tube with a wicking or absorptive material positioned within the gas path. The wicking or absorptive material connects with an external liquid supply or reservoir. Heat is applied to the wicking material, releasing vapour into the tube. Different humidification systems hold liquid within compartments or reservoirs within the tube. Once heat is applied, vapour moves through a permeable membrane into the lumen of the tube.

An external liquid supply reduces the portability of the system, increases the number of set-up steps, and thus increases the overall complexity of the system. The system also requires a large portion of the limited space within a surgical theatre.

Liquid held in reservoirs within the tube increases the weight and reduces the flexibility of the tube, thereby making the tube difficult to manipulate within the surgical space.

BRIEF SUMMARY

A humidification system is disclosed that comprises a tube with an integrated liquid supply and heating mechanism to provide heated and humidified gases to a patient.

In an embodiment, the humidification system comprises a bead that is configured to absorb or hold a liquid. The bead is spirally wound with an outer layer to form a tube. The tube is pre-loaded such that sufficient liquid is stored within the bead. A heating mechanism is integral to the tube and supplies heat to the bead to release vapour and to increase the gases temperature to above ambient temperature. The outer layer provides a barrier to reduce or eliminate the likelihood of the generated vapour entering the atmosphere. Gases flowing through the tube are heated and humidified by the vapour that is released from the bead. Heat is also supplied to the gases by the heating mechanism. The heating mechanism is connected with an external power supply.

The tube comprises a small diameter and lightweight construction. Thus, the humidification system is easily integrated into a surgical environment. Liquid required for the surgical procedure is stored within the bead material. Flexibility of the tube is maintained when liquid is stored within the bead. The liquid is released as vapour upon application of heat. The bead is configured to provide structural support to the tube.

The humidification system comprises minimal set-up steps due to the integrated tube design. For example, there is no need for an external liquid reservoir to supply the system with sufficient liquid for the surgical procedure. Similarly, there is no need for a wick to convey liquid into the tube so that humidification can take place. The tube is not dependent on a specific orientation for functionality, which gives the medical practitioner more freedom to manipulate the system.

According to a first aspect of the present disclosure, a tube for delivering humidified gases is disclosed. The tube comprises a hydrophilic or hygroscopic material and a heating mechanism. The hydrophilic or hygroscopic material stores a liquid in the tube. The heating mechanism heats the liquid stored in the tube to produce vapour to humidify gases delivered by the tube. The tube is pre-loaded by storing liquid in the hydrophilic or hygroscopic material prior to use.

The hydrophilic or hygroscopic material may store sufficient liquid to produce a desired amount of humidity for an intended volume of gases delivered by the tube. The desired amount of humidity may be at least 50% relative humidity. The desired amount of humidity may be at least 80% relative humidity. The hydrophilic or hygroscopic material may be a thermoplastic polyurethane. The hydrophilic or hygroscopic material may be a nylon. The heating mechanism may be a heater wire. The heating mechanism may be integral to the tube. The heating mechanism may be positioned near the centre of the lumen. The heating mechanism may heat gases delivered by the tube.

The tube may comprise an outer layer and a bead of the hydrophilic or hygroscopic material spirally wrapped inside the outer layer. The bead may provide structural support to the outer layer. The outer layer may be spirally wound with the bead. The bead may be positioned internally to the outer layer. The outer layer may have low permeability to liquid, vapour, and/or gases. The outer layer may be a hydrophobic material. The outer layer may be impermeable to liquid, vapour, and gases. The outer layer may be a thermoplastic polyurethane. The heating mechanism may be positioned adjacent to the bead.

According to a second aspect of the present disclosure, a medical gases delivery system for providing heated and humidified gases to a patient during a medical procedure is disclosed. The medical gases delivery system comprises a gases source and a tube for delivering heated and humidified gases from the gases source to the patient. The tube comprises a hydrophilic or hygroscopic material and a heating mechanism. The hydrophilic or hygroscopic material stores liquid in the tube. The heating mechanism heats liquid stored in the tube to produce vapour to humidify gases delivered by the tube. The heating mechanism heats gases delivered by the tube. The tube is pre-loaded by storing liquid in the hydrophilic or hygroscopic material prior to use during the medical procedure.

The hydrophilic or hygroscopic material may store sufficient liquid to produce a desired amount of humidity for an intended volume of gases delivered by the tube. The desired amount of humidity may be at least 50% relative humidity. The desired amount of humidity may be at least 80% relative humidity. The intended volume of medical gases may be a volume sufficient for use during the surgical procedure. The hydrophilic or hygroscopic material may be a thermoplastic polyurethane. The hydrophilic or hygroscopic material may be a nylon. The heating mechanism may be a heater wire. The heating mechanism may be integral to the tube. The heating mechanism may be positioned near the centre of the lumen.

The tube may comprise an outer layer and a bead of the hydrophilic or hygroscopic material spirally wrapped inside the outer layer. The bead may provide structural support to the outer layer. The outer layer may be spirally wound with the bead. The bead may be positioned internally to the outer layer. The outer layer may have low permeability to liquid, vapour, and/or gases. The outer layer may be a hydrophobic material. The outer layer may be impermeable to liquid, vapour, and gases. The outer layer may be a thermoplastic polyurethane. The heating mechanism may be positioned adjacent to the bead.

In some embodiments, an integrated tubular device for delivering humidified gases includes an elongate tubular body comprising an open proximal end, an open distal end, and a lumen therethrough; a material operably connected to an interior of the lumen and configured to reversibly store a volume of liquid in liquid form within the material and release the volume of liquid in vapour form when the material is heated; and a heating element operably connected to the elongate tubular body, the heating element configured to heat the material such that the volume of liquid transforms from a liquid form to the vapour form.

In some embodiments, the material comprises a hydrophilic or hygroscopic material. In some embodiments, the material comprises a hydrophilic material. In some embodiments, the material comprises a hygroscopic material. In some embodiments, the material is configured to absorb the volume of liquid. In some embodiments, the material is configured to wick the volume of liquid. In some embodiments, the material comprises the volume of liquid. In some embodiments, the volume of liquid is between about 10 cc and about 1,000 cc. In some embodiments, the volume of liquid is between about 25 cc and about 500 cc. In some embodiments, the elongate tubular layer comprises an outer layer, wherein the outer layer is impermeable to liquid, vapour, or gases. In some embodiments, the heating element comprises a heater wire. In some embodiments, the heater wire is proximate the material. In some embodiments, the liquid comprises water.

In some embodiments, a method of delivering humidified gases to a target includes providing an integrated tubular device for delivering humidified gases, comprising: an elongate tubular body comprising an open proximal end, an open distal end, and a lumen therethrough; a material operably connected to an interior of the lumen and configured to reversibly store a volume of liquid in liquid form within the material and release the volume of liquid in vapour form when the material is heated: flowing gases from a gases source from the open proximal end of the elongate tubular body, through the lumen, and out the open distal end of the elongate tubular body; heating the material such that at least a fraction of the volume of liquid transforms from a liquid form to the vapor form to humidify the flowing gases; and flowing the humidified gases to the target.

In some embodiments, the method further comprises contacting the material with a source of the liquid to reversibly store the volume of liquid in liquid form within the material. In some embodiments, at least 50% of the volume of liquid transforms from a liquid form to the vapour form to humidify the flowing gases. In some embodiments, wherein the target comprises an operative site of a patient. In some embodiments, the gases comprise carbon dioxide. In some embodiments, the liquid comprises water.

BRIEF DESCRIPTION OF THE DRAWINGS

FIG. 3E illustrates a longitudinal cross-section of another configuration for a tube humidifier.

FIG. 3F illustrates a longitudinal cross-section of another configuration for a tube humidifier.

FIG. 3G illustrates a transverse cross-section of another configuration for a tube humidifier.

FIG. 3H illustrates a longitudinal cross-section of the configuration for the tube humidifier of FIG. 3G.

FIGS. 5-7 illustrate schematics of humidification systems according to at least one embodiment of the disclosed apparatus and systems.

FIGS. 8-9 illustrate longitudinal cross-sections of tube humidifiers for a tube humidification system according to embodiments of the disclosed apparatus and systems.

FIG. 10A illustrates a longitudinal cross-section of a tube humidifier for a tube humidification system according to embodiments of the disclosed apparatus and systems.

FIG. 10B illustrates a transverse cross-section of the tube humidifier of FIG. 10A.

DETAILED DESCRIPTION

Figure 1:
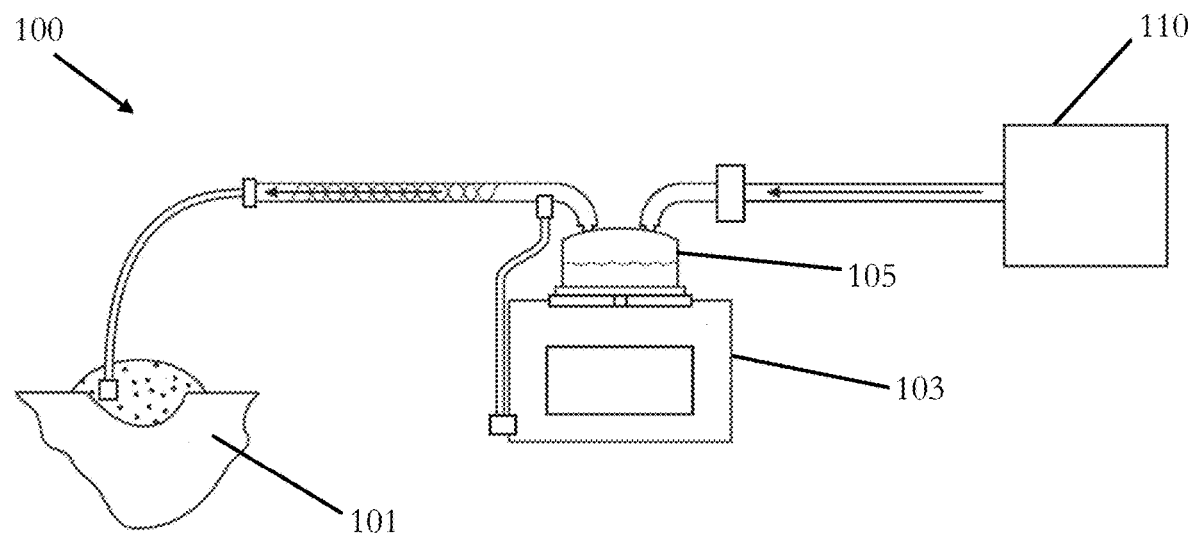
FIG. 1 illustrates a schematic of a conventional humidification system as seen in the prior art.

FIG. 1 illustrates a prior art humidification system 100 that is configured to deliver heated and humidified gases to a patient 101. The humidification system 100 comprises a humidification apparatus 103, a humidification chamber 105, and a gases source 110. In an embodiment, the gases source 110 is an insufflator. The humiditfication chamber 105 is configured to hold water. The humidification apparatus 103 comprises a heating mechanism configured to heat the water within the humidification chamber 105 to form water vapour. Gases from the gases source 110 are heated and humidified as they pass through the humidification chamber 105 and the conditioned gases are delivered to the patient 101.

Gases as herein described refers to respiratory gases (for example, oxygen, air, nitrogen, carbon dioxide, or a combination of any of these), or surgical gases, (for example, carbon dioxide, nitrous, oxygen, air, helium, or a mixture of carbon dioxide with nitrous or oxygen). Other gases or combinations of gases also fall within the scope of the disclosed apparatus and systems.

Figure 2:
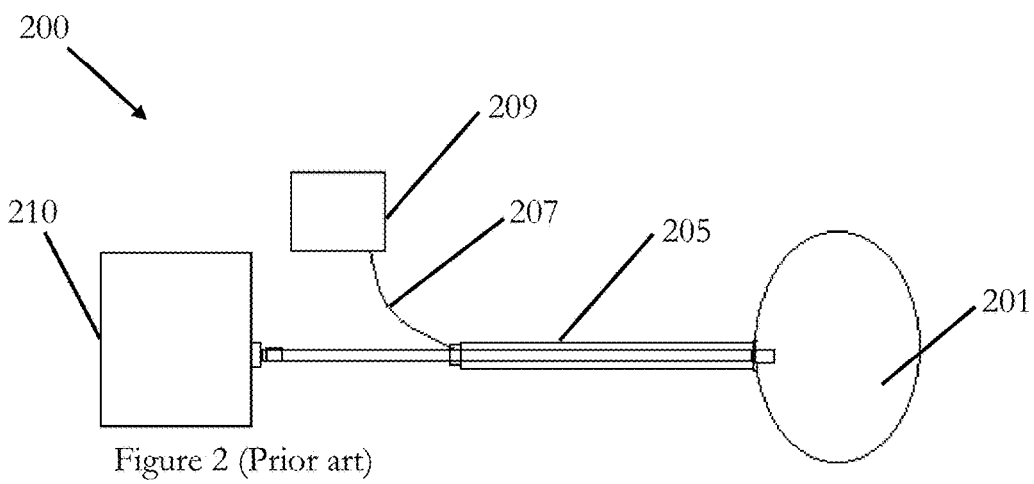
FIG. 2 illustrates a schematic of a tube humidification system as seen in the prior art.

FIG. 2 illustrates a prior art humidification system 200 that is configured to deliver heated and humidified gases to a patient 201. The humidification system 200 comprises a tube humidifier 205, a water channel 207, a water supply 209, and a gases source 210. Gases from the gases source 210 are delivered to the patient 201 via the tube humidifier 205. The tube humidifier 205 comprises a wicking membrane that wicks water via the water channel 207 from the water supply 209. The water that has been wicked is heated using a heating mechanism, thereby causing evaporation of the water. The water vapour generated enters the lumen of the tube humidifier 205, thereby causing the gases flowing therein to become humidified. The humidified gases are delivered to the patient 201.

Figure 3:
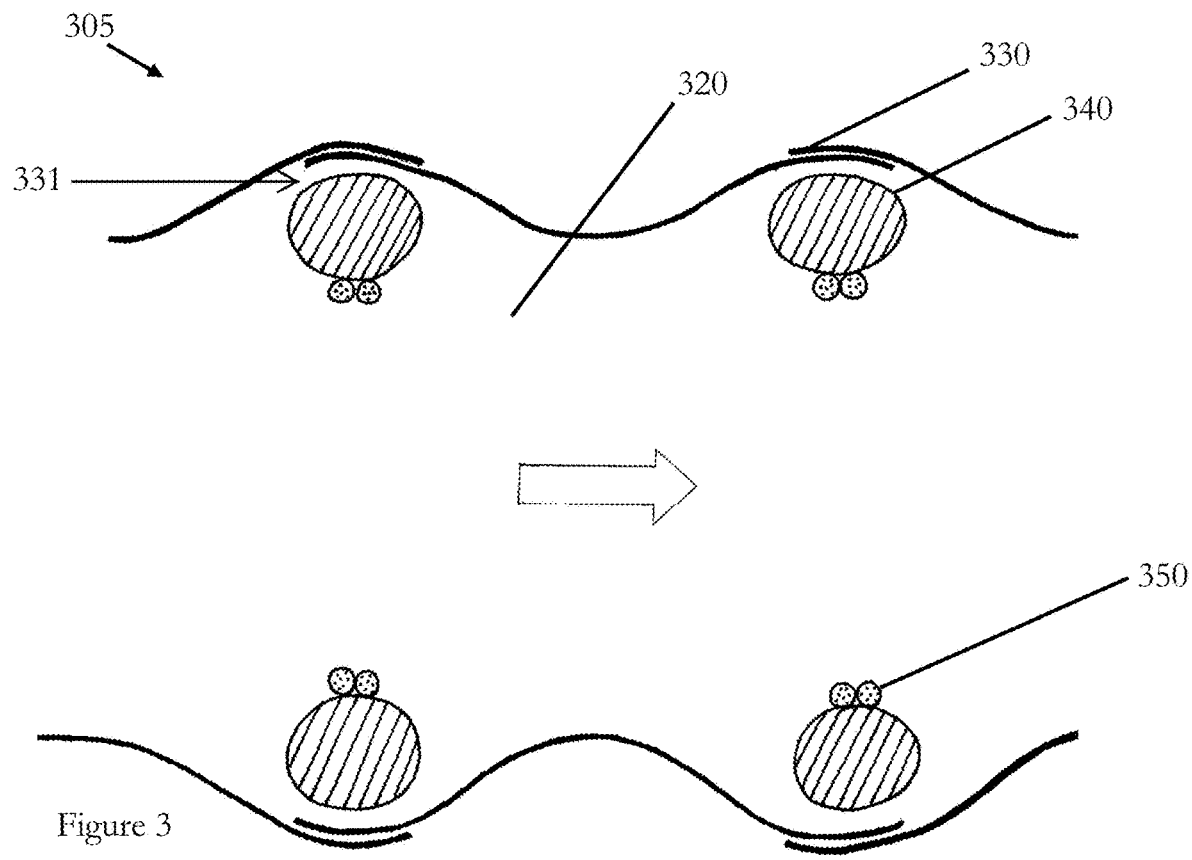
FIG. 3 illustrates a longitudinal cross-section of a tube humidifier for a humidification system according to an embodiment of the disclosed apparatus and systems.

FIG. 3 illustrates an example embodiment of a tube humidifier 305 that is configured to deliver heated and humidified gases to a patient. The tube humidifier 305 can be configured to be a disposable component. The tube humidifier 305 comprises a single component to facilitate heating and humidifying gases. The tube humidifier 305 comprises an outer layer 330, a bead 340, and a heating mechanism 350. The tube humidifier 305, for example, the outer layer 330 of the tube humidifier 305, defines a lumen 320 that is configured to provide a passageway through which gases are transported from the gases source to the patient. The outer layer 330 is configured to provide a barrier between the lumen 320 and the atmosphere. Thus, the outer layer 330 is configured to comprise a low permeability to gases, liquid, and vapour. Low permeability, as herein described refers to a material that provides at least a partial barrier to reduce or eliminate the likelihood of liquid, gases, and/or vapour reaching the atmosphere, such that sufficient gases move through the system to maintain the pneumoperitoneum of the patient.

In an embodiment, the outer layer 330 is made from materials from the class of thermoplastic polyurethanes. In an embodiment, the outer layer 330 comprises polyethylene. In an embodiment, the outer layer 330 comprises polyester. The scope of the disclosed apparatus and systems are in no way limited to the examples above, thus, any suitable or similar material could be used to form the outer layer 330. The outer layer 330 provides a strong, tough, and flexible layer of the tube humidifier 305. In an embodiment, the outer layer 330 is hydrophobic. In an embodiment, the outer layer 330 is not hydrophilic. In an embodiment, the outer layer 330 is configured to be non-permeable to gases, liquid, and vapour.

The bead 340 can be spirally wound, associated in a linear fashion, or otherwise operably connected with the outer layer 330 to form a tube. In an embodiment, the tube comprises an extruded or corrugated configuration. In an embodiment, the tube comprises an annular bead. In an embodiment, the bead 340 is inserted into the lumen 320 of the tube. The bead 340 can be pre-coiled prior to insertion into the lumen 320. The bead 340 can be formed into a plurality of rings and inserted into the lumen 320. In an embodiment, the outer layer 330 of the tube comprises multiple layers wherein the bead 340 is configured to be positioned between the layers. The bead 340 may be bonded to at least one of the layers or may be freely positioned within the layers. In a further embodiment, the bead 340 may be coupled with the outside of the tube. For example, the bead 340 may bond with the outside of the tube. In an additional example, the bead 340 may be pre-coiled such that it can be mechanically fitted to the outside or inside of the tube.

In the illustrated embodiment, the bead 340 comprises a hydrophilic or hygroscopic material. The bead 340 is configured to hold a liquid, for example, water, and/or a medicament. In some embodiments, the bead or other material is configured to hold a volume of liquid such that the volume of liquid does not substantially migrate out of the material until the material is heated as desired. A hygroscopic material can store liquid, such as water, in a liquid form. A hygroscopic material attracts and holds water molecules via adsorption. The material can be porous (like silica gel or zeolite) or can have surface features that increase the effective surface area of the material. A hydrophilic material can store liquid, such as water, in a liquid and/or vapour form. A hydrophilic material stores water via absorption. The material can be foamed or can include surface features to increase the effective surface area of the material.

Prior to use, the tube humidifier 305, e.g., the bead 340, is pre-loaded to facilitate the entry of liquid into the bead 340. In an embodiment, the tube humidifier 305 is soaked prior to use. Thus, the tube humidifier 305 is preloaded with liquid and provided to the medical practitioner ready to use. This improves the usability of the tube humidifier 305 by reducing the number of set-up steps for the system. The quantity of liquid held within the bead 340 is sufficient to supply between 50% to 100% relative humidity during a surgical procedure. In an embodiment, the bead 340 is configured to hold enough liquid to supply humidity for a given volume of gases, in the range of 50% to 80%, 80% to 100%, 90% to 100%, or at least 80% relative humidity during a surgical procedure. Sufficient liquid can be stored within the tube humidifier 305 to provide humidification for a range of volumes of gases required for different surgical procedures. For example, a range of tube humidifiers 305 can be configured to hold a range of quantities of liquid to provide humidification for different surgical procedures. In some embodiments, the relative humidity is delivered at or substantially at body temperature, e.g., about 37° C. In some embodiments, the volume of liquid that can be reversibly stored by the material is between about 10 cc and about 1,000 cc, between about 25 cc and about 500 cc, or between about 50 cc and about 250 cc in some embodiments.

The bead 340 can be made of materials chosen such that the bead 340 is strong and easy to process. In an embodiment, the bead 340 holds liquid using chemical properties such that liquid is stored within the bead 340. Storage of liquid in this way also enables the bead 340 to remain lightweight and flexible. The bead 340 can contribute towards the overall strength and robustness of the tube humidifier 305. In an embodiment, the bead 340 provides a structural component to the tube humidifier 305.

In an embodiment, the tube comprises a bead 340 and a reinforcing component. In such an embodiment, the bead 340 may not provide a structural component to the tube humidifier 305. The reinforcing component can comprise a metal or plastic material. The reinforcing component can comprise, for example, a reinforcing rib and can be positioned within the tube humidifier 305. In an embodiment, the tube humidifier 305 comprises the reinforcing component integrally within the outer layer 330 of the tube humidifier 305. In a further embodiment, the reinforcing component is positioned externally to the tube humidifier 305. In a further embodiment, a heating mechanism 350, discussed in further detail below, comprises the reinforcing component. For example, but without limitation, the heating mechanism 350 may comprise a steel heater wire.

In an embodiment, the materials of the bead 340 are chosen from the class of thermoplastic polyurethanes. In an embodiment, the materials of the bead 340 are chosen from the class of nylons. In a further embodiment, the bead 340 comprises polyester. In a further embodiment, the bead 340 comprises polyether. The scope of the disclosed apparatus and systems is in no way limited to the examples above; thus, any suitable or similar material could be used to form the bead 340.

In an embodiment, materials are chosen that facilitate bonding between the outer layer 330 and the bead 340. In an embodiment, the materials are chosen such that bonding does not occur, or is less likely to occur, between the outer layer 330 and the bead 340. An additional component, for example, an adhesive, a weld, or a mechanical coupling mechanism, may facilitate coupling between the outer layer 330 and the bead 340. In an embodiment, the bead 340 may be positioned freely within the lumen 320 of the tube humidifier 305. In an embodiment, the outer layer 330 may comprise a preformed film. In a further embodiment, the bead 340 is configured to be contained within space that is created by a coaxial tube arrangement. The coaxial tube arrangement comprises an inner tube comprising a gases permeable material and an outer tube comprising a low permeability or gases impermeable material. In an embodiment, the bead 340 bonds to the inner tube. In an embodiment, the bead 340 bonds to the outer tube. In an embodiment, the bead 340 lies freely between the inner tube and the outer tube.

In an embodiment, the bead 340 comprises a circular shape. The bead 340 can have a diameter of approximately 1 mm. In an embodiment, the bead 340 comprises a triangular, square, elliptical or other customised shape. A different diameter of the bead 340 falls within the scope of the disclosed apparatus and systems. Characteristics of the bead 340 can be chosen to optimise performance. In an embodiment, the characteristics can be chosen to meet the requirements of different surgical procedures.

In an embodiment, the diameter of the bead 340 is chosen to optimise absorption or total absorbed liquid volume of the bead 340. For example, increasing the diameter of the bead 340 may increase the absorption level of the bead 340 for a given material. Similarly, the diameter of the bead 340 is chosen to optimise desorption or the total amount of liquid volume that is released from the bead 340 under given conditions. For example, increasing the diameter of the head 340 may increase the desorption level of the bead 340 under given conditions. The given conditions may comprise, for example, an application of heat to the bead 340.

In an embodiment, the length of the tube is chosen to meet the requirements of different surgical procedures. For example, the tube can be 3 m in length. Altering the length of the tube, for example, to 2 m or 4 m in length, or to other lengths as specified by the surgical procedure, falls within the scope of the disclosed apparatus and systems.

Altering the surface area of the bead 340 may alter the rate of absorption for a given material. Altering the surface area of the bead 340 may also alter the rate of desorption and thus the rate at which liquid is released from the bead 340.

Altering the pitch of the bead 340 may alter the volume of liquid that is absorbed by the bead 340 for a given length of tube. For example, for a given material a tighter pitch facilitates a greater quantity of liquid being stored within the bead 340 as compared with the volume of liquid stored within a bead comprising a larger pitch. Therefore, the pitch can be optimised to control the volume of liquid stored within the bead 340.

Altering the material of the bead 340 can alter the performance, for example, absorption capacity, rate of absorption, and/or rate of desorption. In an embodiment, materials can be chosen to optimise the absorption capacity of the bead 340. In an embodiment, materials can be chosen to optimise the rate of absorption or the rate of desorption of the bead 340.

Figures 4A, 4B, 4C:
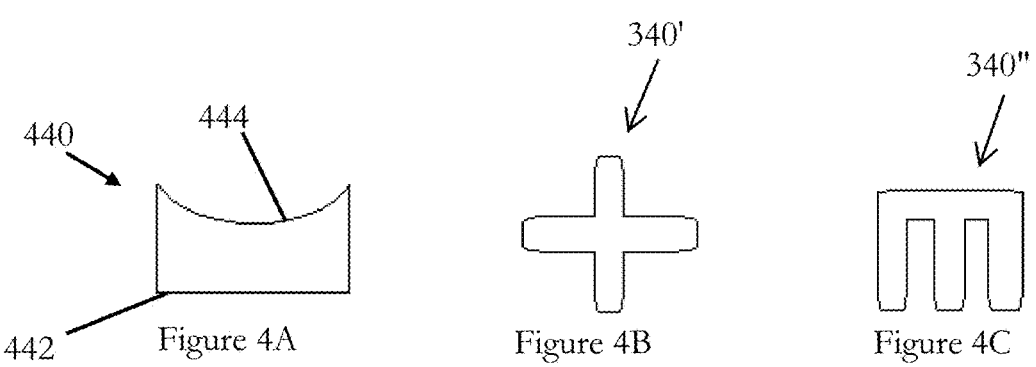
FIGS. 4A-4C illustrate cross-sections of a component of a tube humidification system according to at least one embodiment of the disclosed apparatus and systems.

In an embodiment, liquid is trapped in a pocket 331 that forms near the bonding location between the bead 340 and the outer layer 330. The shape of the bead 340 can be chosen to determine the angle between the bead 340 and the outer layer 330, which can be chosen to optimise the volume of liquid trapped therein. The trapped liquid is vaporised upon application of heat by the heating mechanism 350. Altering the shape of the bead 340 can affect liquid movement within the bead 340. In the illustrated example embodiment of FIG. 4A, a bead 440 comprises a square base 442 and a concave top 444, herein referred to as a cup shape. The cup shape is configured to trap liquid FIGS. 4B and 4C illustrate embodiments of beads 340', 340" that increase the surface area of the beads 340', 340" relative to bead 340 to improve, e.g., increase, the rate of absorption and the rate of desorption. Increasing the surface area increases the time that gases contact the bead 340', 340", thereby increasing the humidification of the gases as they pass through the tube humidifier 305. The embodiments shown in FIGS. 4A-4C are examples only and other shapes and configurations also fall within the scope of the disclosed apparatus and systems.

In the illustrated embodiment, the bead 340 comprises a non-foamed material. In an embodiment, the bead 340 comprises a foamed material. A foamed material facilitates increased liquid absorption and increased surface area for moisture and heat transfer within the tube humidifier 305. The foamed material creates voids within which the liquid is held in addition to the liquid held within the material. Thus, the material has an increased liquid uptake compared with a non-foamed material. The material remains breathable such that the liquid is easily released from the voids. A foamed material may be used in procedures requiring a large amount of relative humidity, for example, due to usage of a large volume of gases. The foamed material is configured to be pre-loaded with liquid prior to use. In an embodiment, the foamed material is soaked to take up liquid prior to use. In an embodiment, the foamed material is injected with liquid prior to use.

Heat is applied to the bead 340 to heat the gases to a temperature that is greater than the ambient temperature and to release liquid stored within the bead 340. Released vapour enters the lumen 320 and humidifies the gases flowing through the tube humidifier 305. Release of vapour into the lumen 320 is controlled by the amount of heat supplied to the bead 340. A heating mechanism 350 is located near the bead 340 and acts to apply heat to the bead 340. In an embodiment, the heating mechanism 350 is integral with the bead 340. In an embodiment, the heating mechanism 350 is adjacent the bead 350. In a further embodiment, the heating mechanism 350 is positioned within the lumen 320 of the tube. In an embodiment in which the outer layer 330 comprises multiple layers, the heating mechanism 350 can be positioned between layers. In an embodiment, the heating mechanism 350 can be positioned external to (e.g., wrapped around an outer surface of) the outer layer 330, in such an embodiment, the heating mechanism 350 can be insulated.

In an embodiment, the tube comprises a dry section and a humidifying section. For example, the humidifying section comprises a bead 340 to humidify the gases. The dry section comprises a non-humidifying section. Thus, gases move through the dry section, into the humidifying section, where they are humidified prior to delivery to the patient. The humidifying section comprises the heating mechanism 350. In an embodiment, the dry section comprises the heating mechanism 350 to heat the gases prior to entry into the humidifying section. This may improve the desorption rate of vapour from the bead 340. In an embodiment, the dry section is an unheated section. In an embodiment, the gases move through the humidifying section, into the dry section, and to the patient. Thus, the humidifying section and the dry section may comprise the heating mechanism 350 such that heated humidified gases are provided to the patient. Heating within the dry section causes a decrease in the relative humidity of the gases, which reduces the likelihood of condensate formation as the gases reach the patient. Thus, heating within the dry section of the tube may improve control of the temperature drop between the heated tube and the patient to reduce the condensate formed within the system. In a further alternative embodiment, multiple dry and humidifying sections are interspersed along the length of the tube. In an embodiment, multiple heating wires allow for customised heating solutions. For example, low or no heating can be applied in parts of the tube and increased heating can be applied in other parts of the tube.

In the illustrated embodiment of FIG. 3, the heating mechanism 350 comprises a heater wire. In an embodiment, multiple heater wires are used, for example, two heater wires. The heater wires may be coated prior to being positioned near the bead 340. The diameter and material of the heater wires affects the resistance of the heater wires. In the illustrated embodiment, the diameter of the heater wires is 0.22 mm. The diameter can be chosen to optimise the resistance of the heater wires and to affect the power delivered to the system. Thus, a range of different diameters and materials fall within the scope of the disclosed apparatus and systems.

The heating mechanism 350 can be integrated into the tube. The pitch of the heating mechanism 350 affects the distribution of heat produced. For example, a smaller pitch causes a more equal distribution of heat within the tube compared to a larger pitch. The pitch is optimised to provide sufficient heat and relative humidity to the gas for a given procedure. In an embodiment, the heating mechanism 350 is incorporated within the bead 340. In an embodiment, the heating mechanism 350 is positioned on the inner surface of the bead 340. This reduces the surface temperature of the tube humidifier 305. Thus, the tube humidifier 305 is more comfortable to the touch. In an embodiment, the surface temperature of the tube humidifier 305 is configured to fall within acceptable limits as specified by Medical Design Standard IEC60601. A power supply (discussed below) supplies power to the heating mechanism 350.

The power supply delivers power to the heating mechanism 350, which is integrated with the tube humidifier 305. In some embodiments, a control system is configured to control the power, and subsequently heat, delivered to the tube humidifier 305, causing the gases to be heated to above ambient temperature and humidity to be released from the bead 340. The amount of heat delivered is determined based on the power supplied to the system. This enables the control system to make an estimation of the humidity being received by the patient. In an embodiment, the control system supplies differential heating to the system to control or adjust the temperature and humidity of the gases that are delivered to the patient.

The control system is configured to initiate a warm up mode. The warm up mode is configured to last for the duration of the warm up of other surgical instruments, such as, for example, a scope warmer or a cannula. The warm up mode can be controlled such that the dew point temperature of the gases within the tube humidifier 305 exceeds the temperature of the surgical instruments, thus reducing condensate formation. In the illustrated embodiment, no additional sensors or other form of feedback are required. In an embodiment, sensors such as a humidity sensor, temperature sensor, flow sensor, and/or pressure sensor could be used to control the system.

In an embodiment, the control system and the power supply are integrated into a single component. The single component may be integrated into the tube humidifier 305 or may be an external component. In an embodiment, the control system and the power supply comprise individual or separated components. In a further embodiment, the control system is integrated into a gases source. In a further embodiment, the control system is integrated into a connector. In a further embodiment, the control system is integrated into the tube humidifier 305.

Figure 3A:
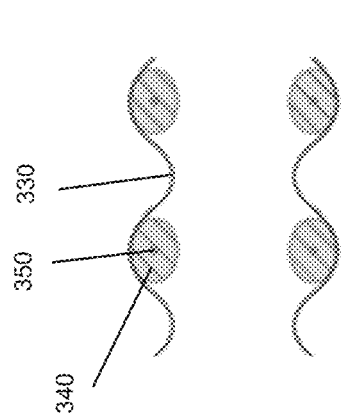
FIG. 3A illustrates a transverse cross-section of a configuration for a tube humidifier.
Figure 3B:
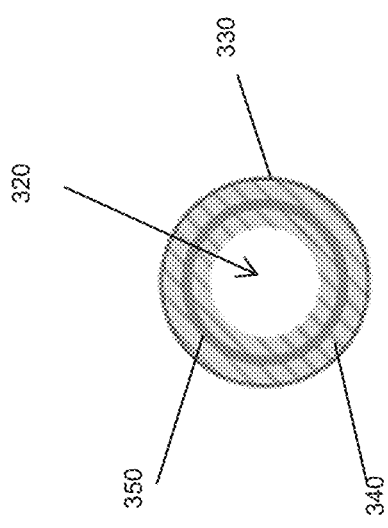
FIG. 3B illustrates a longitudinal cross-section of the configuration for the tube humidifier of FIG. 3A.
Figure 3C:
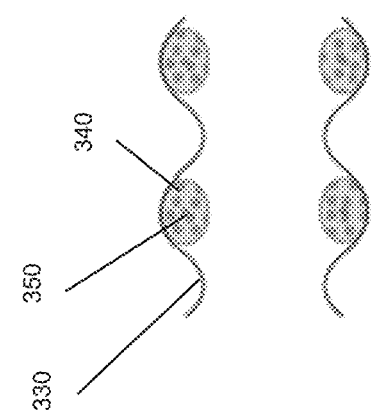
FIG. 3C illustrates a longitudinal cross-section of another configuration for a tube humidifier.
Figure 3D:
FIG. 3D illustrates a longitudinal cross-section of another configuration for a tube humidifier.

FIGS. 3A-3H illustrate various configurations for the tube humidifier 305. In the embodiment of FIGS. 3A-3B, the heating mechanism 350 is a heater wire disposed within and surrounded by the bead 340. In the illustrated embodiment, the bead 340 is positioned adjacent and/or attached to the outer layer 330 and is spirally wound or formed in rings disposed within the outer layer 330. FIG. 3C illustrates a configuration in which the material of the bead 340 is foamed as described herein, which can advantageously increase the storage capacity of the bead 340 and/or allow for quicker pre-loading (absorption or adsorption) of the bead 340. In some embodiments, for example as shown in FIG. 3D, diameters of the tube (e.g., of the outer layer 330) and/or the bead 340 can be increased relative to other configurations to increase the storage capacity of the bead 340 and/or strength of the tube. In some embodiments, a diameter of the bead 340 can be approximately 1.5 mm. In some embodiments, a diameter of the tube can be approximately 10 mm. FIG. 3E illustrates a configuration similar to that of FIGS. 3A-3B in which the bead 340 is formed of a different material e.g., Estane, which may increase the storage capacity of the bead 340 compared to the material of the bead 340 of FIGS. 3A-3B, which may be, for example, Arnitel. In some embodiments, for example as shown in FIG. 3F, a reinforcing wire 341 can be disposed within and surrounded by the bead 340 to help strengthen the tube. In some embodiments, the reinforcing wire 341 is made of stainless steel. FIGS. 3G-3H illustrate an example configuration similar to that of FIGS. 3A-3B; however, in the configuration of FIGS. 3G-3H, the bead 340 is separated from the outer layer 330 by a layer of liquid 332. In some embodiments, the layer of liquid 332 can act as a reservoir to store additional liquid that can permeate into the bead 340 as the liquid pre-stored in the bead 340 is vaporized in use. In some embodiments, the separation of the bead 340 from the outer layer 330 allows for easier manufacturing and assembly. For example, the bead 340 and the outer layer 330 can be extruded or otherwise formed independently from one another and then assembled together, for example, by coiling the bead 340 and inserting the bead 340 into the outer layer 330. The bead 340 can be soaked with liquid before or after insertion into the outer layer 330. Other configurations and materials for the bead 340 and/or heater wire 350 are also possible.

Figure 5:
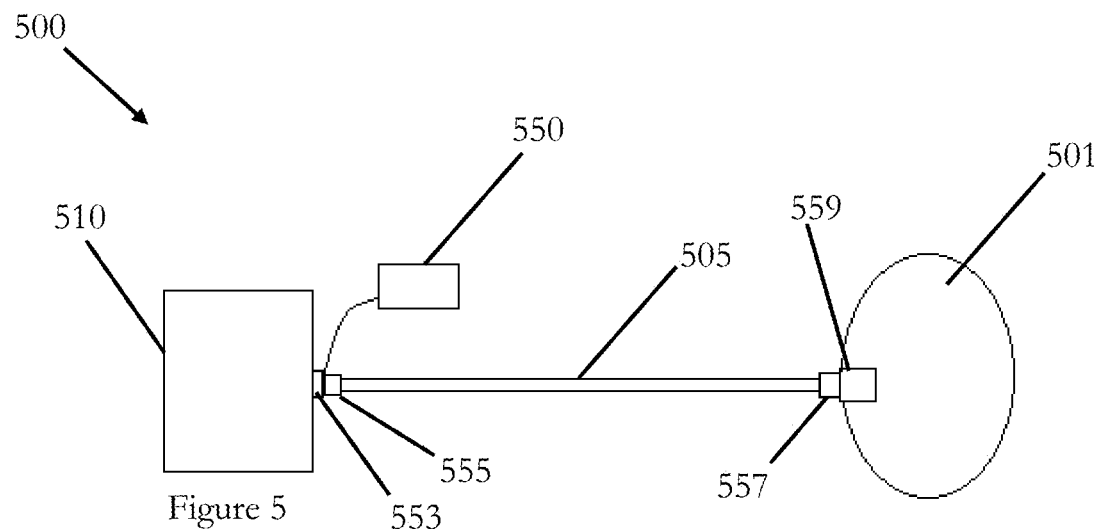
Figure 6:
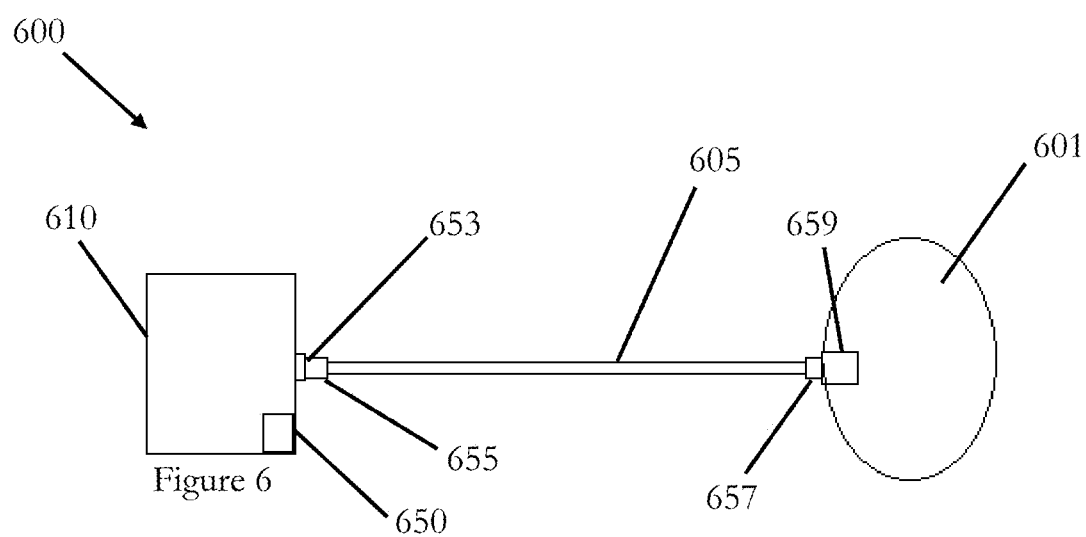

FIGS. 5-7 illustrate example embodiments of systems incorporating a tube humidifier, which can include some or all of the features of the tube humidifier 305 described herein and shown in FIG. 3.

FIG. 5 illustrates an example embodiment of a humidification system 500 that delivers gases to a patient 501. The humidification system 500 comprises a tube humidifier 505 according to the present disclosure, a gases source 510, a power supply 550, a first connector 555, and a second connector 557 connecting with a patient interface 559. The tube humidifier includes a heating mechanism as described herein, for example, heating mechanism 350. The humidification system 500 can also include a filter 553. The power supply 550 is configured to supply power to the heating mechanism within the tube humidifier 505. The first connector 555 enables an electrical connection to be formed between the power supply 550 and the heating mechanism. The power supply 550 is located externally to the tube humidifier 505. The power supply 550 is configured to be a reusable component. A cable connects the power supply 550 to the first connector 555.

In the illustrated embodiment, the tube humidifier 505 connects directly to the gases source 510 via the first connector 555, thereby forming a pneumatic connection. An electrical connection is formed between the power supply 550 and the tube humidifier 505 through the first connector 555. In an embodiment, the power supply 550 couples with the tube humidifier 505 at any point along the length of the tube humidifier 505. In such an embodiment, an additional connector can form an electrical connection between the power supply 550 and the tube humidifier 505. The power supply 550 is a compact unit that is easily integrated into the medical environment.

FIG. 6 illustrates an example embodiment of a humidification system 600 that delivers heated and humidified gases to a patient 601. The humidification system 600 comprises a tube humidifier 605 according to the present disclosure, a gases supply 610, a power supply 650, a first connector 655, and a second connector 657 connecting with a patient interface 659. The tube humidifier includes a heating mechanism as described herein, for example, heating mechanism 350. The humidification system 600 can also include a filter 653. The power supply 650 is configured to supply power to the heating mechanism within the tube humidifier 605. In the illustrated embodiment, the power supply 650 is integrated with the gases source 610. The power supply 650 is configured to be a reusable component. The first connector 655 enables an electrical and pneumatic connection between the gases source 610 and the tube humidifier 605.

The tube humidifier 305, 505, 605 thus has improved ease of use over the humidification systems 100, 200 disclosed above and illustrated in FIGS. 1 and 2. The tube humidifier 305, 505, 605 has a similar footprint to a conventional tube set, while providing humidified gases to the patient. Use of a small diameter tube, for example, a tube with a diameter of approximately 8 mm, reduces the footprint of the tube humidifier 305, 505, 605. In an embodiment, the diameter of the tube can be chosen to maintain sufficient compressible volume within the system. In an embodiment, the tube humidifier 305, 505, 605 comprises a different diameter tube. Selecting the desired diameter alters the footprint of the tube humidifier 305, 505, 605 as appropriate. The length of the tube should be sufficient for use in the surgical environment. In an embodiment, the length is approximately 3 m. In an embodiment, the length is approximately 2.5 m. Longer or shorter tubes also fall within the scope of the disclosed apparatus and systems.

FIG. 7 illustrates an example embodiment of a humidification system 700 that delivers heated and humidified gases to a patient 701. The humidification system 700 comprises a tube humidifier 705 according to the present disclosure, a gases source 710, a power supply 750, a first connector 755, and a second connector 757 that connects with a patient interface 759. The tube humidifier includes a heating mechanism as described herein, for example, heating mechanism 350. The humidification system can also include a filter 753. The power supply 750 is integrated into the tube humidifier 705. The power supply 750 comprises, for example, a battery source. In an embodiment, the power supply 750 is a disposable product. In an embodiment, the power supply 750 is removably coupled to the tube humidifier 705. Thus, the power supply 750 can be a reusable product. The battery source is replaceable following a surgical procedure.

In the illustrated embodiment, the power supply 750 connects via connector 755 to the gases source 710. The electrical connection between the power supply 750 and the tube humidifier 705 can be formed via the connector 755. A pneumatic connection is formed between the tube humidifier 705 and a gases source 710 using the connector 755. In an embodiment, the power supply 750 is located on an external surface of the tube humidifier 705. The power supply 750 forms an electrical connection between an additional connector connected with the cable of the power supply 750 and a junction on the external surface of the tube humidifier 705.

In an embodiment, the tube humidifier 305, 505, 605, 705 may comprise an integrated sensing system for improved control. In an additional embodiment, two sensor wires are incorporated with the heating mechanism 350. The sensing system may comprise an end of hose sensor. In an embodiment, sensor probes provide an indication of the gases characteristics. Characteristics such as humidity, temperature, flow, and/or pressure could be sensed using the sensing system.

In an embodiment, alternative power supplies, such as batteries or standard electrical systems, can be used to supply power to the tube humidifier 305, 505, 605, 705. In an embodiment, the power supply comprises an indication of liquid using visual cues, for example, light emitting diodes, warning lights, or a colour change. The visual cues can be achieved by electromechanical, mechanical or chemical mechanisms. By way of example only, silica is red when dry and turns blue when saturated by a liquid, such as, water. In an embodiment, the visual cues are displayed on the first connector 555, 655, 755, or the second connector 557, 657, 757, as discussed, or on an outer surface of the tube humidifier 305, 505, 605, 705.

In an embodiment, the heating mechanism 350 comprises alternative mechanisms, for example, exothermic reactions, induction heating or electromagnetic heating.

In an embodiment, for example as shown in FIG. 8, a tube humidifier 805 may comprise an outer layer 830 that comprises multiple layers to improve insulation. In an embodiment, the multiple layers may comprise spaces between them, for example, comprising air, to further improve the insulation properties.

Figure 9:
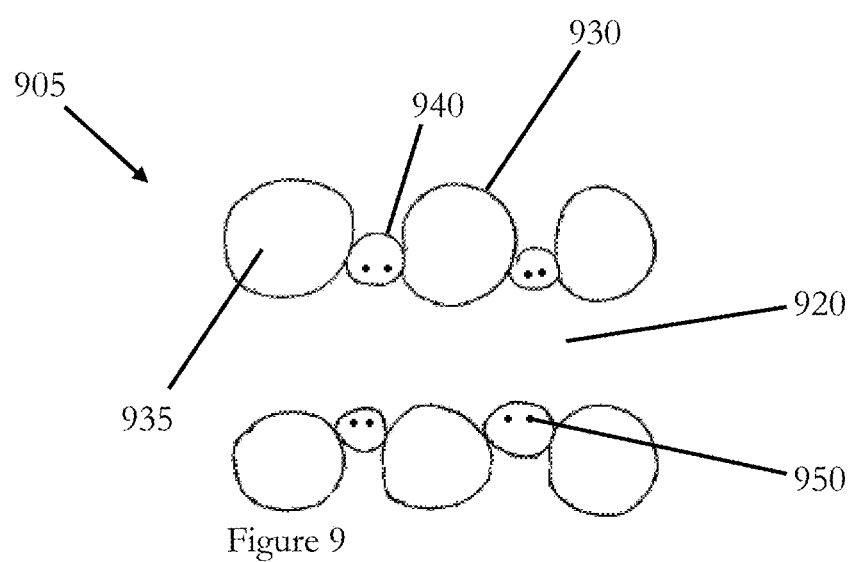

In an embodiment, for example as shown in FIG. 9, a tube humidifier 905 comprises an outer layer 930 that comprises a hollow tube 935 that is spirally wound defining a lumen 920 of a larger tube. In an embodiment, the hollow tube 935 is wound with a bead 940 to form a larger tube. The hollow tube 935 provides properties such as insulation and flexibility to the larger tube. The bead 940 provides a structural component to the larger tube. In an embodiment, the hollow tube 935 provides a structural component and the bead 940 provides insulation and flexibility to the larger tube. In an embodiment, a heating mechanism 950 is integral to the tube. In an embodiment, the heating mechanism 950 is incorporated within the hollow tube 935. In an embodiment, the heating mechanism 950 is incorporated within the head 940.

FIGS. 10A and 10B illustrate an embodiment of a tube humidifier 1005 that comprises a heating mechanism, such as one or more heater wires 1050, insulated in and surrounded by one or more layers of a hydrophilic or hygroscopic material 1040. In some embodiments, the material 1040 can be Arnitel (a thermoplastic co-polyester). In some embodiments, the material 1040 can be Estane (a thermoplastic polyurethane). The tube humidifier 1005 comprises an outer layer 1030 that defines a lumen 1020 through which gases flow during use. The outer layer 1030 can be similar to (e.g., be made of the same or similar materials, have the same or a similar structure, etc.) other outer layers as described herein. For example, the outer layer 1030 can be non-permeable or have a low permeability to gases (e.g., surgical gases), liquids, and/or vapour.

The layer of material 1040 holds a liquid, such as water and/or a medicament. The material 1040 can store and hold the liquid, such as water or saline, via a chemical bond. For example, due to the polarity of water, water can chemically bond to the material. In use, heat from the heater wire 1050 causes the liquid to vaporize and be released from the material 1040 (or causes a vapour stored in the material 1040 to be released) into the lumen 1020 where the vapour mixes with and humidifies gases flowing through the lumen 1020 to the patient. The material 1040 can be permeable to the vapour in all directions. In other words, the material can release the liquid in the form of vapour in all directions and is not orientation dependent. This allows for gases passing over or by any portion of the material 1040 to be humidified. The release of liquid from the material 1040 can be dependent on a temperature and/or concentration gradient between the material 1040 and the surrounding environment. In some such embodiments, a heater wire 1050 may not be needed to drive release of liquid from the material 1040. In some embodiments, the amount of liquid released (in the form of vapour) and/or the rate of liquid released during the procedure can be controlled by controlling the power to the heater wire 1050. The heater wire 1050 may be the only heating mechanism in a humidification system including the tube humidifier 1005. The heater wire 1050 can therefore affect or control the temperature and/or humidity of gases delivered to the patient. The relative humidity and efficiency of such a humidification system is therefore a function of the tube humidifier 1005 geometry (e.g, the surface area of the material 1040 exposed to the gases flowing through the tube humidifier 1005), the contact time between the gases and the hydrophilic material, the temperature of the gases, and/or the energy supplied by the heater wire 1050.

The material 1040 can be pre-soaked or pre-loaded with the liquid. The material 1040 can be pre-soaked with a known quantity of liquid, which may be a quantity of liquid calculated or determined to be needed during a particular laparoscopic procedure of a particular duration. A humidification system incorporating the tube humidifier 1005 therefore need not include a separate, external liquid reservoir or delivery system and as such the reversible liquid reservoir can advantageously be integrated within the tube itself. The user may not need to input liquid into the system before or during the procedure. Properties such as the diameter of the layer of material 1040 and/or the amount of the material 1040 present can be adjusted to adjust the quantity of liquid that can be stored in the layer of material 1040. Adjusting the diameter or amount of material 1040 may alter the amount of liquid that can be held by the material 1040, but may affect the inner diameter of the tube humidifier 1005 or the space available for gases to flow within the lumen 1020, which may in turn affect resistance to gases flow within the tube humidifier 1005. For example, increasing the diameter of the layer of material 1040 for an outer layer 1030 having a given diameter can decrease the space available for gases flow between the layer of material 1040 and the outer layer 1030, which can increase resistance to gas flow within the tube humidifier 1005, but allows the material 1040 to hold more liquid. Thus, a trade-off exists between the quantity of liquid held by the material 1040 and the resistance to flow. If desired, a diameter or length of the tube humidifier 1005 can be altered to balance these effects.

In some embodiments, the layer of material 1040 and/or heater wire 1050 can extend along an entire length of the tube humidifier 1005 from an insufflator to the patient. In other embodiments, the layer of material 1040 and/or heater wire 1050 maybe extend along only part or parts of the length of the tube humidifier 1005. The layer of material 1040 and heater wire 1050 can be free floating within the outer layer 1030. In some embodiments, the layer of material 1040 and/or heater wire 1050 can be secured at a connector between the tube humidifier 1005 and the insufflator, a connector between the tube humidifier 1005 and the patient, and/or at one or more points along the tube humidifier 1005, for example, to maintain the layer of material 1040 and/or heater wire 1050 generally in a centre of tube humidifier 1005.

In some embodiments, the heater wire 1050 (or heater wires 1050 if the tube humidifier 1005 includes multiple heater wires 1050) extends longitudinally within the layer of material 1040 and the tube. In other embodiments, the heater wire 1050 (or wires) extends within the layer of material 1040 and the tube in a spiral configuration. In some embodiments, both the heater wire 1050 and the surrounding layer of material 1040 can extend along the tube in a spiral configuration. A spiral configuration can increase the surface area exposed to surgical gases flowing through the tube. In some embodiments, instead of or in addition to a heater wire within the layer of material 1040, a heating mechanism, such as a heater wire, can be embedded within the outer layer 1030, disposed on or wrapped around an inner or outer surface of the outer layer 1030, or disposed within the lumen 1020 outside of the layer of material 1040.

The layer of material 1040 can be made of various materials, such as those described herein with respect to bead 340. The rate of liquid uptake by the layer of material 1040 during loading is dependent on, for example, the amount of surface contact of the material 1040 to the liquid, the temperature of the liquid (e.g., hot water is generally taken up faster than cold water), and/or the time of exposure of the material 1040 to the liquid. If desired or required, the material can be selected to increase the amount of water held by the layer of material 1040. However, increasing the amount of water held may increase the weight of the tube humidifier 1005 due to the increased weight of the additional water and because a greater amount and therefore weight of material is generally needed to hold a greater amount of water. A given material may be able to hold only a small percentage of its weight in water. Therefore, to increase the amount of water held, a relatively large increase in material weight may be required. In some embodiments, the layer of material 1040 can be rechargeable, for example, by re-soaking the layer of material 1040 in the liquid.

In some embodiments, the layer of material 1040 can have cavities or channels within the material. Such cavities or channels can increase the liquid-storage capacity of the layer of material 1040. The cavities or channels can be pre-loaded with liquid. In some embodiments, the cavities or channels can be rechargeable, for example, during use or between uses. Smaller cavities or channels may have an increased resistance to loading and storing liquid, whereas larger cavities or channels may have a decreased resistance to loading and storing liquid. In some embodiments, the layer of material 1040 has multiple cavities or channels. In some embodiments, the tube humidifier 1005 includes multiple layers of material 1040. Each layer may include one or more cavities or channels. In some embodiments having multiple layers of material 1040, each layer may include, e.g., sur-round, a heater wire 1050. In other embodiments, multiple layers may surround a single heater wire 1050.

Figure 11B:
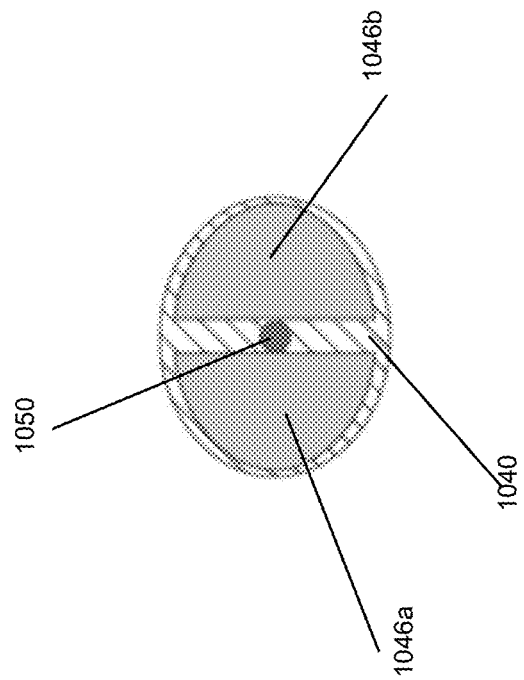
FIG. 11B illustrates a transverse cross-section of a configuration for components of a tube humidifier.
Figure 11A:
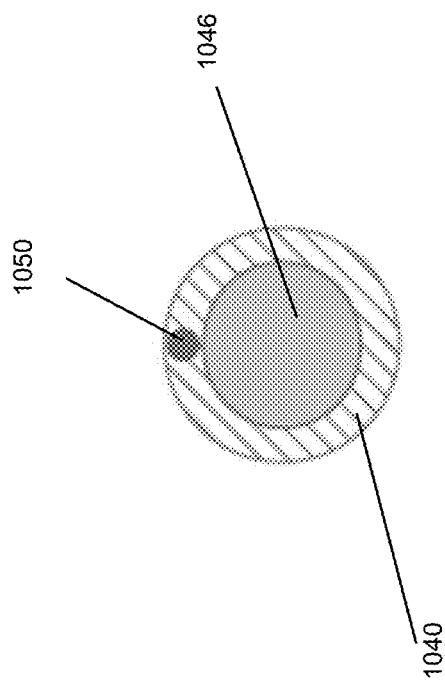
FIG. 11A illustrates a transverse cross-section of a configuration for components of a tube humidifier.

In some embodiments, the tube humidifier 1005 can include one or more layers of a hydrophilic or hygroscopic material 1040 surrounding a central liquid reservoir or channel 1046, with a heating mechanism, such as one or more heater wires 1050, disposed in the layer(s) of material 1040, for example as shown in FIG. 11A. Such an arrangement may allow for quicker manufacturing as the central liquid channel 1046 may be able to be filled more quickly than the material 1040 can be pre-soaked. Liquid can permeate the material 1040 from the channel 1046. The heater wires 1050 can extend longitudinally within the material 1040, can extend in a spiral along a length of the material 1040, or be arranged in other configurations. FIG. 11B illustrates an alternative arrangement in which the layer(s) of material 1040 surrounds two liquid reservoirs or channels 1046*a*, 1046*b* and the heating mechanism, such as one or more heater wires 1050, is positioned in a central reinforcing strut portion or the material 1040. Such an arrangement can advantageously help liquid from the liquid reservoirs 1046*a*, 1046*b* permeate the material 1040 more quickly.

In some embodiments, the tube humidifier 1005 includes a wick in contact with the layer of material 1040. In some embodiments, the wick can be at least partially placed within a channel in the layer of material 1040. The wick can allow for transfer of liquid from a reservoir (e.g., channel 1046 shown in FIG. 11A or a separate reservoir used to load the material 1040) to the hydrophilic material, for example, before use, for recharging, and/or during use. The use of a wick and reservoir can increase the overall liquid storage and release capacity of the layer of material 1040 during use.

The tube humidifier 1005 can be incorporated into humidification systems such as those described herein. Such systems can include a control system, which may be external to the tube humidifier 1005. Such systems can include a power source external to the tube humidifier 1005 for supplying power to the heater wire 1050 and/or to the control system.

The tube humidifier 1005, and other tube humidifiers described herein and according to the present disclosure, can advantageously allow for a humidification system with a smaller footprint and fewer set-up steps than prior art systems.

Although reference has been made throughout this specification regarding surgical procedures, such as open or laparoscopic surgery, the disclosed apparatus and systems can be applied to different medical fields, for example, respiratory assistance systems.

It should be noted that various changes and modifications to the presently preferred embodiments described herein will be apparent to those skilled in the art. Such changes and modifications may be made without departing from the spirit and scope of the apparatus and systems of the disclosure and without diminishing its attendant advantages. For instance, various components may be repositioned as desired. It is therefore intended that such changes and modifications be included within the scope of the apparatus and systems of the disclosure. Moreover, not all of the features, aspects and advantages are necessarily required to practice the present apparatus and systems of the disclosure. Accordingly, the scope of the present apparatus and systems of the disclosure is intended to be defined only by the claims that follow.

Reference to any prior art in this specification is not, and should not be taken as, an acknowledgement or any form of suggestion that that prior art forms part of the common general knowledge in the field of endeavour in any country in the world.

Wherein the foregoing description reference has been made to integers or components having known equivalents thereof, those integers are herein incorporated as if individually set forth.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The apparatus and system of the disclosure may also be said broadly to include the parts, elements and features referred to or indicated in the specification of the application, individually or collectively, in any or all combinations of two or more of said parts, elements or features.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "humidifying a target region" includes "instructing the humidifying of a target region." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An integrated tubular device for delivering humidified gases, the integrated tubular device comprising:
    an elongate tubular body comprising an open proximal end, an open distal end, and a lumen there through;
    a material operably connected to an interior of the lumen and configured to reversibly store a volume of liquid in a liquid form within the material and release the volume of liquid in a vapour form when the material is heated, the material being spirally wound or formed in rings, portions of the elongate tubular body extending radially inward toward a center of the lumen between adjacent turns of the spirally wound or rings of the material, the material contacting an interior surface of the elongate tubular body to provide structural support to the elongate tubular body; and
    a heating element in a form of a helix operably connected to the elongate tubular body, the heating element within the material and extending along a length of the spirally wound or rings of the material such that the heating element is surrounded by the material, the heating element configured to heat the material such that the volume of liquid transforms from the liquid form to the vapour form.

2. The device of claim 1, wherein the material comprises a hydrophilic or hygroscopic material.

3. The device of claim 1, wherein the material comprises a hydrophilic material.

4. The device of claim 1, wherein the material comprises a hygroscopic material.

5. The device of claim 1, wherein the material is configured to absorb the volume of liquid.

6. The device of claim 1, wherein the material is configured to wick the volume of liquid.

7. The device of claim 1, wherein the material comprises the volume of liquid.

8. The device of claim 1, wherein the volume of liquid is between about 10 cc and about 1,000 cc.

9. The device of claim 1, wherein the volume of liquid is between about 25 cc and about 500 cc.

10. The device of claim 1, wherein the elongate tubular body comprises an outer layer, wherein the outer layer is configured to be impermeable to liquid, vapour, or gases.

11. The device of claim 1, wherein the heating element comprises a heater wire.

12. The device of claim 1, wherein the liquid comprises water.

13. A method of delivering humidified gases to a target using the integrated tubular device of claim 1, the method comprising:
    flowing gases from a gases source from the open proximal end of the elongate tubular body, through the lumen, and out the open distal end of the elongate tubular body;
    heating the material such that at least a fraction of the volume of liquid transforms from the liquid form to the vapour form to humidify the flowing gases; and
    flowing the humidified gases to the target.

14. The method of claim 13, further comprising reversibly storing the volume of liquid in the liquid form within the material.

15. The method of claim 13, wherein at least 50% of the volume of liquid transforms from the liquid form to the vapour form to humidify the flowing gases.

16. The method of claim 13, wherein the target comprises an operative site of a patient.

17. The method of claim 13, wherein the gases comprise carbon dioxide.

18. The method of claim 13, wherein the liquid comprises water.

19. The device of claim 1, wherein the material is configured as a bead.

20. The device of claim 1, wherein the material and the elongate tubular body together define a wall of the integrated tubular device, the wall extending from the open proximal end to the open distal end of the elongate tubular body.

21. The device of claim 1, wherein the heating element in the form of a helix is extending along an entire length of the elongate tubular body.

* * * * *